United States Patent
Lee et al.

(10) Patent No.: US 10,947,316 B2
(45) Date of Patent: *Mar. 16, 2021

(54) ANTIBODY-DRUG CONJUGATES CONTAINING ANTI-GLOBO H ANTIBODIES AND USES THEREOF

(71) Applicant: Development Center for Biotechnology, New Taipei (TW)

(72) Inventors: Chao-Pin Lee, New Taipei (TW);
Shih-Hsien Chuang, New Taipei (TW);
Chuan-Lung Hsu, New Taipei (TW);
Yi-Jen Chen, New Taipei (TW);
Yu-Chin Nieh, New Taipei (TW);
Win-Yin Wei, New Taipei (TW);
Chia-Cheng Wu, New Taipei (TW)

(73) Assignee: Development Center for Biotechnology, New Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 16/010,251

(22) Filed: Jun. 15, 2018

(65) Prior Publication Data

US 2019/0106507 A1 Apr. 11, 2019

Related U.S. Application Data

(60) Provisional application No. 62/520,484, filed on Jun. 15, 2017.

(51) Int. Cl.

| *A61P 35/00* | (2006.01) |
| *A61K 47/68* | (2017.01) |
| *A61K 49/00* | (2006.01) |
| *G01N 33/574* | (2006.01) |
| *A61K 47/64* | (2017.01) |
| *A61K 47/65* | (2017.01) |
| *A61K 31/337* | (2006.01) |
| *A61K 31/5365* | (2006.01) |
| *C07K 16/30* | (2006.01) |
| *A61K 39/395* | (2006.01) |
| *C07K 16/28* | (2006.01) |

(52) U.S. Cl.
CPC ........ *C07K 16/3015* (2013.01); *A61K 39/395* (2013.01); *A61K 47/6425* (2017.08); *A61K 47/65* (2017.08); *A61K 47/6803* (2017.08); *A61K 47/6809* (2017.08); *A61K 47/6851* (2017.08); *A61K 47/6855* (2017.08); *A61K 47/6857* (2017.08); *A61K 47/6859* (2017.08); *A61K 47/6865* (2017.08); *A61K 47/6887* (2017.08); *A61K 47/6898* (2017.08); *A61K 49/0041* (2013.01); *A61K 49/0058* (2013.01); *A61P 35/00* (2018.01); *C07K 16/28* (2013.01); *C07K 16/30* (2013.01); *C07K 16/303* (2013.01); *C07K 16/3023* (2013.01); *C07K 16/3053* (2013.01); *G01N 33/57492* (2013.01); *A61K 31/337* (2013.01); *A61K 31/5365* (2013.01); *G01N 2400/02* (2013.01)

(58) Field of Classification Search
CPC ........ A61K 39/001173; A61K 47/6887; A61K 49/0058; A61K 47/6803; G01N 33/57492; G01N 2400/02

See application file for complete search history.

(56) References Cited

U.S. PATENT DOCUMENTS

| 2004/0037833 A1* | 2/2004 | Mather | A61P 25/00 424/155.1 |
| 2015/0344551 A1* | 12/2015 | Wong | C07K 16/18 424/133.1 |
| 2016/0102151 A1* | 4/2016 | Wong | C07K 16/18 424/135.1 |

FOREIGN PATENT DOCUMENTS

WO   WO-2018218068 A1 * 11/2018 .............. A61P 35/00

* cited by examiner

*Primary Examiner* — Karen A. Canella
(74) *Attorney, Agent, or Firm* — Liang Legal Group, PLLC

(57) ABSTRACT

An immunoconjugate includes an anti-Globo H antibody, or a binding fragment thereof, and a therapeutic agent or a label, having the formula: $Ab-(L-D)_m$, wherein Ab is the anti-Globo H antibody or the binding fragment thereof, L is a linker or a direct bond, D is the therapeutic agent or the label, and m is an integer from 1 to 8. The antibody may be a monoclonal antibody, which may be a humanized antibody. A method for treating a cancer includes administering to a subject in need of such treatment a pharmaceutically effective amount of an immunoconjugate containing an antibody against Globo H, or a binding fragment thereof, and a therapeutic agent covalently conjugated with the antibody.

12 Claims, 5 Drawing Sheets

Specification includes a Sequence Listing.

MS Analysis of DCBD16001

(A) Internalization of DCBD16001 (HCC-1428)

(B) Internalization of DCBD16001 (MCF-7)

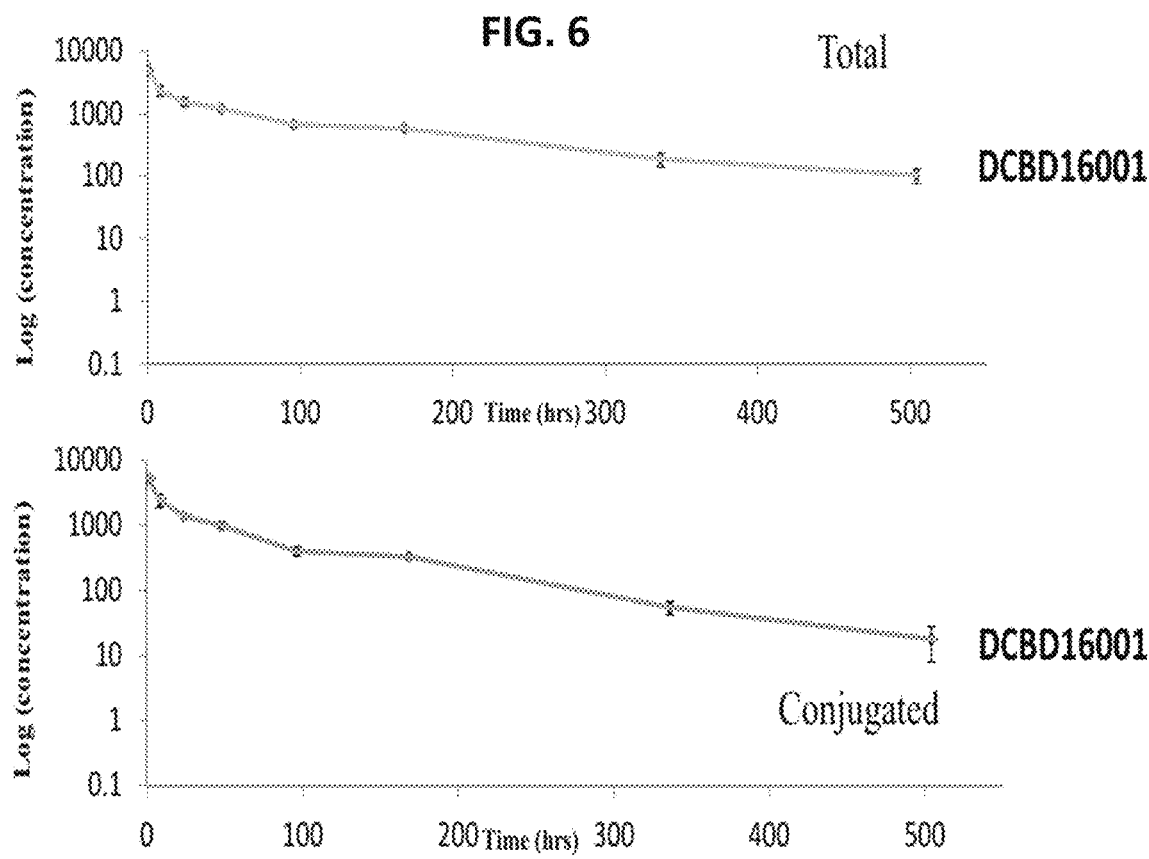
FIG. 6
FIG. 7
Assessments:
1. Body weight will be monitored three times per week.
2. Tumor volume will be measured by caliper three times per week.
3. Survival rate will be observed (if necessary).
4. At the end of the experiment, tumor weight will be measured and serum and tumor tissues will be collected.
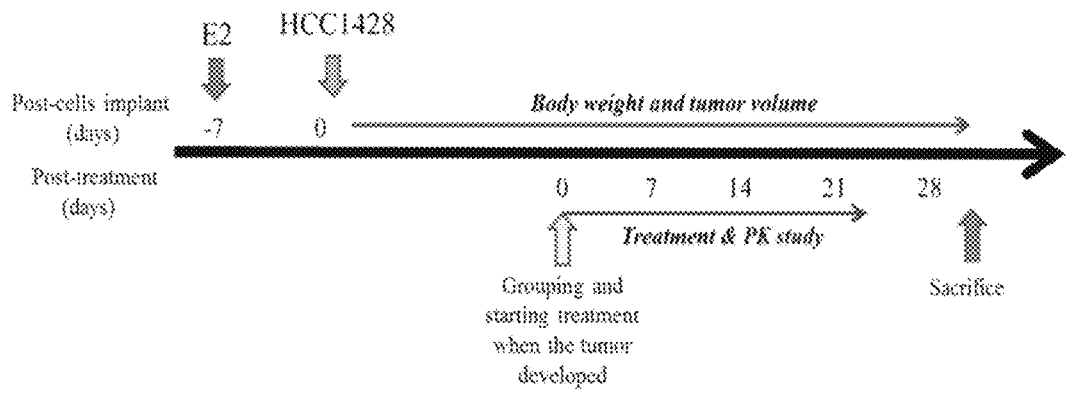

Tumor Growth Inhibition in HCC-1428 Model

DCBD16001 in HCC1428

SEQUENCE LISTING

```
<160> NUMBER OF SEQ ID NOS: 6

<210> SEQ ID NO 1
<211> LENGTH: 10
<212> TYPE: PRT
<213> ORGANISM: Mus musculus

<400> SEQUENCE: 1

Gly Tyr Ile Ser Ser Asp Gln Ile Leu Asn
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Synthetic
```

```
<220> FEATURE:
<221> NAME/KEY: MISC_FEATURE
<222> LOCATION: (12)..(12)
<223> OTHER INFORMATION: X is any amino acid

<400> SEQUENCE: 2

Arg Ile Tyr Pro Val Thr Gly Val Thr Gln Tyr Xaa His Lys Phe Val
1               5                   10                  15

Gly

<210> SEQ ID NO 3
<211> LENGTH: 6
<212> TYPE: PRT
<213> ORGANISM: Artificial Sequences
<220> FEATURE:
<223> OTHER INFORMATION: Synthetic

<400> SEQUENCE: 3

Gly Glu Thr Phe Asp Ser
1               5

<210> SEQ ID NO 4
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: X at position 8 is F, Y, or W
<220> FEATURE:
<221> NAME/KEY: MISC_FEATURE
<222> LOCATION: (15)..(15)
<223> OTHER INFORMATION: X at position 15 is C, G, S, or T

<400> SEQUENCE: 4

Lys Ser Asn Gln Asn Leu Leu Xaa Ser Gly Asn Arg Arg Tyr Xaa Leu
1               5                   10                  15

Val

<210> SEQ ID NO 5
<211> LENGTH: 7
<212> TYPE: PRT
<213> ORGANISM: Mus musculus

<400> SEQUENCE: 5

Trp Ala Ser Asp Arg Ser Phe
1               5

<210> SEQ ID NO 6
<211> LENGTH: 9
<212> TYPE: PRT
<213> ORGANISM: Mus musculus

<400> SEQUENCE: 6

Gln Gln His Leu Asp Ile Pro Tyr Thr
1               5
```

ANTIBODY-DRUG CONJUGATES CONTAINING ANTI-GLOBO H ANTIBODIES AND USES THEREOF

BACKGROUND OF INVENTION

Field of the Invention

The present invention relates to antibody-drug conjugates containing Globo H antibodies and their uses in therapy.

Background Art

Antibody-drug conjugates (ADCs) can provide targeted therapy to treat various diseases or conditions, such as cancer. ADCs are complex molecules comprising antibodies linked to biologically active agents, such as cytotoxic agents or drugs. By combining unique targeting of the antibodies with the therapeutic effects of the drugs, antibody-drug conjugates can distinguish between normal and cancer cells, thereby minimizing the side effects.

ADC typically comprises an anticancer drug (e.g. a cytotoxin) coupled to an antibody that specifically targets a marker, e.g., a tumor marker. Antibodies track these proteins down in the body and attach themselves to the surface of cancer cells. The binding between the antibody and the target protein (antigen) triggers a signal in the tumor cell, which then internalizes the ADC. After the ADC is internalized, the cytotoxic drug may be released and kills the cancer. Due to the specific targeting, the drug has lower side effects.

Globo H is a hexasaccharide belonging to a large number of tumor-associated carbohydrate antigens that are overexpressed on the surface of various epithelial cancer cells, including breast, colon, ovarian, pancreatic, lung, and prostate cancer cells. Therefore, Globo H is a promising diagnostic/therapeutic target.

Although antibodies against Globo H are useful, there remains a need for improved therapeutic agents using anti-Globo H antibodies.

SUMMARY OF INVENTION

The present invention relates to antibody-drug conjugates containing Globo H antibodies and their uses in therapy.

One aspect of the invention relates to immunoconjugates. An immunoconjugate in accordance with one embodiment of the invention includes an anti-Globo H antibody, or a binding fragment thereof, and a therapeutic agent or a label, having the formula: Ab–(L–D)$_m$, wherein Ab is the anti-Globo H antibody or the binding fragment thereof, L is a linker or a direct bond, D is the therapeutic agent or the label, and m is an integer from 1 to 8.

In accordance with any embodiment of the invention, the Ab may comprise a heavy-chain variable domain having three complementary regions consisting of HCDR1 (GYISSDQILN, SEQ ID NO:1), HCDR2 (RIYPVTGVTQYXHKFVG, SEQ ID NO:2, wherein X is any amino acid), and HCDR3 (GETFDS, SEQ ID NO:3), and a light-chain variable domain having three complementary regions consisting of LCDR1 (KSNQNLLX'SGNRRY-ZLV, SEQ ID NO:4, wherein X' is F, Y, or W, and Z is C, G, S or T), LCDR2 (WASDRSF, SEQ ID NO:5), and LCDR3 (QQHLDIPYT, SEQ ID NO:6).

The linker, L, can be a direct bond, in which the payload, D, is directly linked (conjugated) with the antibody or the binding fragment thereof. A linker can be any linker commonly used in protein modification or conjugation, such as a short peptide (e.g., gly-gly-gly), a short organic molecule linker (e.g., SMCC, succinimidyl-4(N-maleimidomethyl) cyclohexane-1-carboxylate), or the like.

The payload, D, can be a therapeutic agent, such as a cytotoxic agent. Examples of ytotoxic agents that may be used with embodiments of the invention may include a maytansinoid (e.g., DM1 or DM4), monomethyl auristatin E (MMAE), monomethyl auristatin F (MMAF), paclitaxel, or the like.

The payload, D, can be a label or agent for diagnosis or imaging. Example of an imaging agent may include DTPA (Diethylenetriaminepentaacetic acid) or DOTA (1,4,7,10-tetraazacyclododecane-1,4,7,10-tetraacetic acid).

In accordance with some embodiments of the invention, the antibody may be a monoclonal antibody, which may be a humanized antibody.

One aspect of the invention relates to methods for diagnosing or imaging cells or a tissue expressing Globo H. A method in accordance with one embodiment of the invention may comprise administering to a subject an immunoconjugate described above.

One aspect of the invention relates to methods for treating cancers. A method in accordance with one embodiment of the invention may comprise administering to a subject in need of cancer treatment a pharmaceutically effective amount of an immunoconjugate described above. The cancer is an epithelial cell cancer, such as breast cancer, colon cancer, ovarian cancer, pancreatic cancer, lung cancer, or prostate cancer.

One skilled in the art would appreciate that a pharmaceutically effective amount depends on many factors, such as patient conditions, age, disease states, routs of administration, etc., and that such effective amount may be determined based on these factors in routine practice without undue experimentation.

Other aspect of the invention will become apparent with the following description.

BRIEF DESCRIPTION OF THE DRAWINGS

FIG. 6 shows the results from the in vivo pharmacokinetic studies of DCBD16001.

FIG. 7 shows the treatment protocol in a cancer xenograft model using an ADC of the invention.

DETAILED DESCRIPTION

Figure 1:
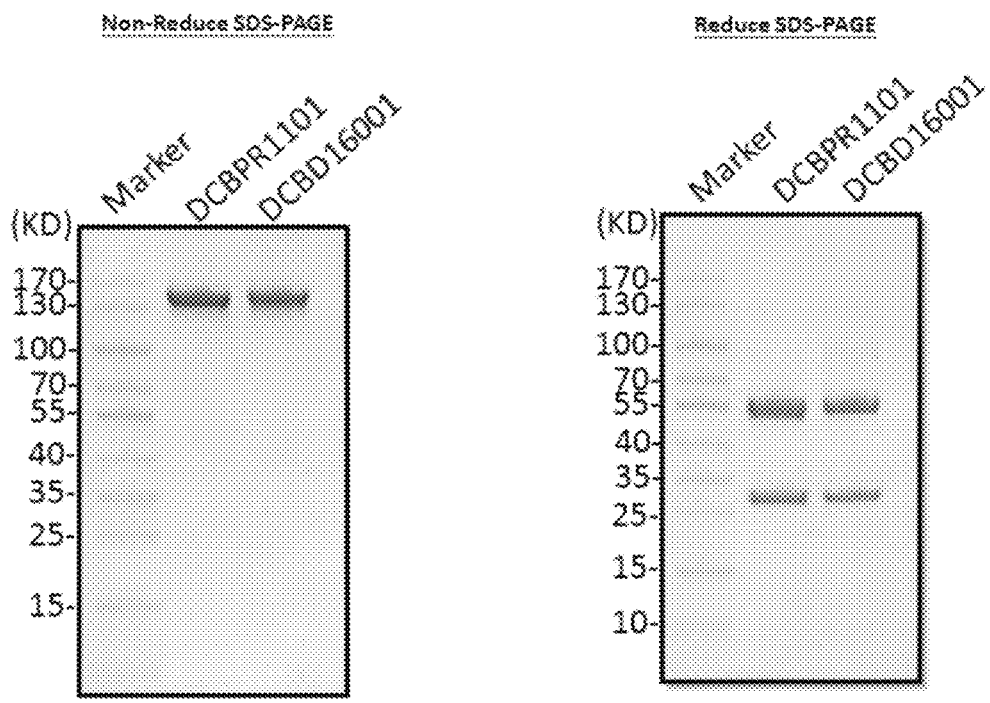
FIG. 1 shows SDS-PGAE gel analysis of an ADC (DCB16001) in accordance with one embodiment of the invention. The results show that the ADC retains the proper antibody structures—i.e., proper molecular weights under non-reduced and reduced conditions.

Embodiments of the invention relate to antibody-drug conjugates containing Globo H antibodies and their uses in therapy. Globo H is a hexasaccharide belonging to a large number of tumor-associated carbohydrate antigens that are overexpressed on the surface of various epithelial cancer cells, including breast, colon, ovarian, pancreatic, lung, and prostate cancer cells. Therefore, ADCs based on antibodies against Glob H can be useful diagnostic and/or treatment agents.

However, the fast internalization or lacking ADCC activity of therapeutic antibody might result in antibody ineffective as well as resistance. Therefore, there is a need to enhance the therapeutic efficacy of anti-Globo H based therapeutics. One approach is to conjugate a payload with an anti-Globo H antibody (i.e., an antibody-drug conjugate). By conjugating anti-Globo H antibodies to payloads (i.e., ADCs), embodiments of the invention are more potent than the naked anti-Globo H antibodies, thereby enabling one to use less antibodies.

In accordance with embodiments of the invention, Globo H antibodies, or a binding fragment thereof, may be coupled to a drug, diagnostic agent, or a therapeutic agent. Thus, the term "antibody-drug conjugate" (ADC) as used herein may refer to an antibody portion (which can be a whole antibody or a binding fragment thereof) coupled to a payload (which can be a drug, a diagnostic agent or a therapeutic agent).

The ADCs of the invention contain payloads designed for the therapeutic or diagnostic uses. These ADCs have better biological activities and would require less amounts to achieve the desired effects, as compare with the naked Globo H antibodies.

Embodiments of the invention will be illustrated with the following specific examples. One skilled in the art would appreciate that these examples are for illustration only and that other modifications and variations are possible without departing from the scope of the invention.

EXAMPLES

Unless otherwise indicated, each $^1$H NMR data were obtained at 500 MHz. The abbreviations used herein are as follows, unless specified otherwise:

Bu: butyl; Bn: benzyl; BOC: t-butyloxycarbonyl; BOP: benzotriazol-1-yloxy tri/dimethylamino-phosphonium hexafluorophosphate; DCC: dicyclohexylcarbodiimide; DMF: N,N-dimethylformamide; DMAP: 4-dimethylaminopyridine; EDC: 1-(3-dimethylaminopropyl) 3-ethylcarbodiimide hydrochloride; EtOAc: ethyl acetate; Eq.: equivalent(s); HOBt: hydroxybenztriazole; LAH: lithium aluminum hydride; MeOH: methanol; MHz megahertz; MS(ES): mass spectrophotometer-electron spray; NMP: N-methylpyrrolidinone; Ph: phenyl; Pr: propyl; TEA: triethylamine; THF: tetrahdrofuran; TLC: thin layer chromatography; Tetrakis tetrakis(triphenylphosphine)palladium.

Example 1. Preparation of Anti-Globo H Antibody

In accordance with embodiments of the invention, a general method for the generation of anti-Globo H antibodies include obtaining a hybridoma producing a monoclonal antibody against Globo H. Methods for the production of monoclonal antibodies are known in the art and will not be elaborated here. Briefly, mice are challenged with antigen (Globo H) with an appropriate adjuvant. Then, the spleen cells of the immunized mice were harvested and fused with hybridoma. Positive clones may be identified for their abilities to bind Globo H antigen, using any known methods, such as ELISA.

Antibody-drug conjugates (ADCs) of the invention can specifically target Globo H. These ADCs can use any antibody that binds specifically to Glob H. For example, ADCs of the invention may use a mouse or humanized anti-Globo H antibody, or an scFv or Fab fragment thereof. An exemplary anti-Globo H antibody may comprise a heavy-chain variable domain having three complementary regions consisting of HCDR1 (GYISSDQILN, SEQ ID NO:1), HCDR2 (RIYPVTGVTQYXHKFVG, SEQ ID NO:2, wherein X is any amino acid), and HCDR3 (GETFDS, SEQ ID NO:3), and a light-chain variable domain having three complementary regions consisting of LCDR1 (KSNQNLLX'SGNRRYZLV, SEQ ID NO:4, wherein X' is F, Y, or W, and Z is C, G, S or T), LCDR2 (WASDRSF, SEQ ID NO:5), and LCDR3 (QQHLDIPYT, SEQ ID NO:6).

In accordance with embodiments of the invention, the antibodies may be mouse antibodies. Alternatively, the antibodies may be chimeric antibodies (e.g., human constant regions coupled to the mouse variable regions) or humanized antibodies (e.g., mouse CDRs grafted on the framework regions of human immunoglobulins) or completely human antibodies.

The monoclonal antibody may be humanized by obtaining the CDR sequences from the hybridoma and cloning the CDR sequences into human framework sequences to produce humanized antibodies. Any common methods known in the art for identifying CDR sequences may be used. The CDR regions in this invention are identified with the Kabat number scheme. First, a hybridoma of anti-Globo H (e.g., mouse GBH hybridoma) was generated. Such a hybridoma may be generated with standard protocols for the production of monoclonal antibodies. The total RNA of the hybridoma was then isolated, for example using the TRIzol® reagent. Then, cDNA was synthesized from the total RNA, for example using a first strand cDNA synthesis kit (Superscript III) and an oligo(dT$_{20}$) primer or an Ig-3' constant region primer.

Heavy and light chain variable regions of the immunoglobulin genes were then cloned from the cDNA. For example, the VH and VL variable regions of the anti-Globo H mAb were amplified from mouse GBH hybridoma cDNAs by PCR, using a mouse Ig-5' primer set (Novagen). The PCR products may be cloned directly into a suitable vector (e.g., a pJET1.2 vector) using CloneJet™ PCR Cloning Kit (Ferments). The pJET1.2 vector contains lethal insertions and will survive the selection conditions only when the desired gene is cloned into this lethal region. This facilitates the selection of recombinant colonies. Finally, the recombinant colonies were screened for the desired clones, the DNAs of those clones were isolated and sequenced. The immunoglobulin (IG) nucleotide sequences may be analyzed at the international ImMunoGeneTics information system (IGMT) website.

Antibody Expression and Purification

For antibody production, the isolated clones may be expressed in any suitable cells. As an example, F293 cells (Life technologies) were transfected with the anti-Globo H mAb expressing plasmid and cultured for 7 days. The anti-Globo H antibody was purified from the culture medium using a protein A affinity column (GE). Protein concentrations may be determined with a Bio-Rad protein assay kit and analyzed with 12% SDS-PAGE, using procedures known in the art or according to the manufacturer's instructions.

In accordance with embodiments of the invention, any of these anti-Globo H antibodies may be used to prepare antibody-drug conjugates (ADCs), as illustrated in the following examples.

Example 2. Preparation of Anti-Globo H Antibody-Biotin Conjugates

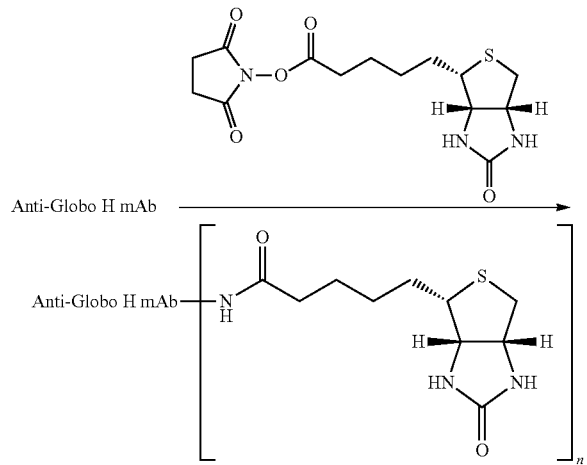

As examples for coupling drugs to antibodies, biotin-avidin system may be used to explore the reaction conditions and to illustrate the workability of the ADC strategies. In this particular example, an analog of biotin (i.e., biotin-N-succinimide ester) is used as a coupling reagent to react with an amino group on the antibodies. The amino group may be a side chain of a lysine residue on the antibody.

Briefly, to a solution of Anti-Globo H monoclonal antibody 430 µL (2.7 mg/mL) in buffer (50 mM potassium phosphate, 50 mM sodium chloride, 2 mM EDTA; pH 6.5) was slowly added 3.8 µL Osu-Biotin (biotin-O-succinimide; 20 mM in DMSO). The reaction mixture was stirred under argon at room temperature and stirred for 2, 4, and 16 hours, respectively. Desalt and concentrate the antibody preparation using the Amicon Ultra-15 centrifugal filter device with 30 kDa NMWL in pH 7.4 PBS buffer to give Globo H-biotin ADC 2-1.

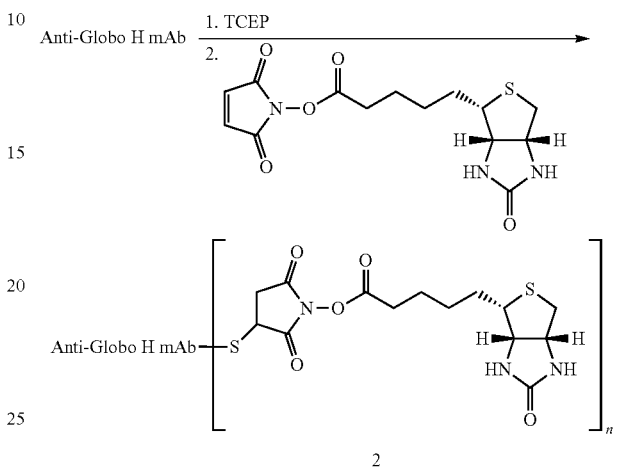

In an alternative approach, the biotin analog may be coupled to an SH group of a cysteine residue on an antibody. As shown in the above reaction scheme, to a solution of Anti-Globo H monoclonal antibody 180 µL (5.0 mg/mL in pH 7.4 PBS buffer) was slowly added TCEP (5.0 eq) and stirred at 37° C. for 1.0 hour. The reaction mixture was then added biotin-maleimide (12 eq) and stirred under argon under room temperature for 20 hours. Desalt and concentrate the antibody preparation using the Amicon Ultra-15 centrifugal filter device with 30 kDa NMWL in pH 7.4 PBS buffer to give Globo H-biotin ADC 2-2.

Example 3. Preparation of Anti-Globo H Antibody-SMCC-DM1 Conjugates

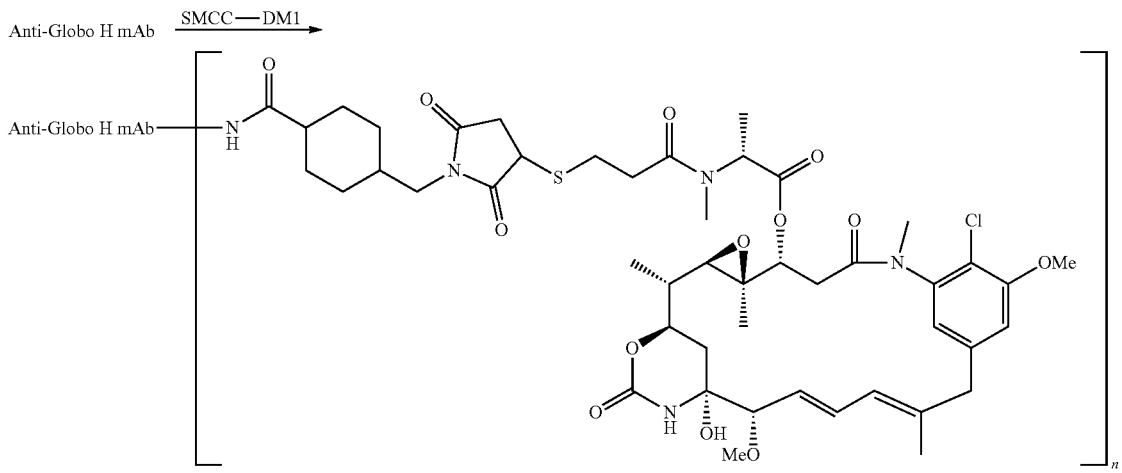

In this example, ADC contains DM1, which is a maytansinoid that was developed for cancer therapy. Maytansine, a benzoansamacrolide, is a highly potent microtubule-targeted compound that induces mitotic arrest and kills tumor cells at subnanomolar concentrations. DM1 binds at the tips of microtubules to suppress the dynamicity of microtubules, i.e., inhibiting the assembly of microtubules. DM1 is a maytansinoid with less systemic toxicity than maytansine. In this example, SMCC-DM1, which is DM1 with a reactive linker SMCC, is used to react with antibody to make antibody drug conjugates. SMCC-DM1 is available from commercial sources, such as MedKoo Biosciences, Inc. or ALB Technology.

For example, to a solution of Anti-Globo H monoclonal antibody 500 μL (2.9 mg/mL) in buffer (50 mM potassium phosphate, 50 mM sodium chloride, 2 mM EDTA; pH 6.5) was slowly added 58 μL SMCC-DM1 (5 mM in DMSO). The reaction mixture was stirred under argon at 37° C. and stirred for 20 hours. Desalt and concentrate the antibody preparation using the Amicon Ultra-15 centrifugal filter device with 30 kDa NMWL in pH 7.4 PBS buffer to give Anti-Globo H-SMCC-DM1 ADC 3. (DCBD16001)

Example 4. Preparation of Anti-Globo H Antibody-SMCC-DM4 Conjugates

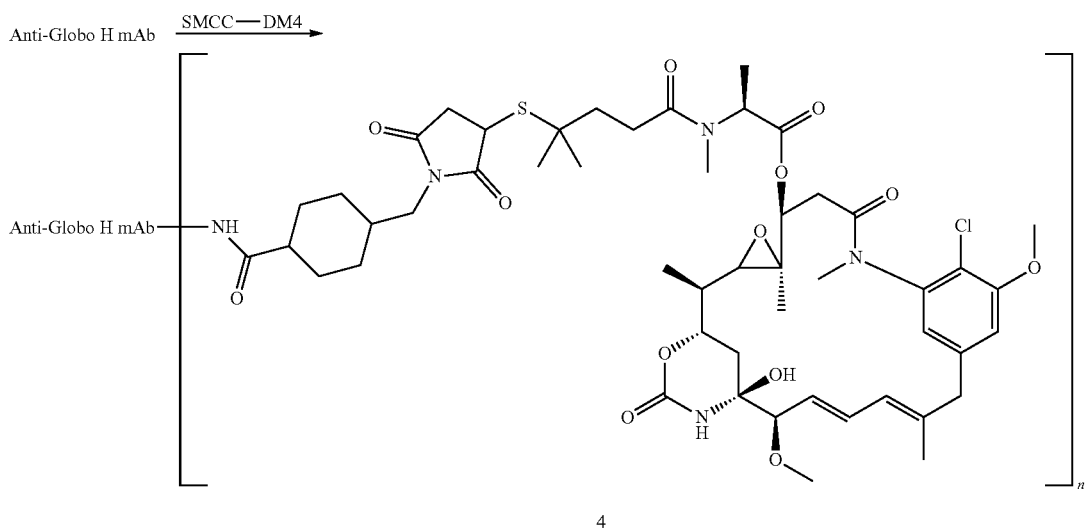

4

DM4 is another maytansine analog. DM4 is also a potent microtubule-targeted compounds that inhibit proliferation of cells at mitosis. Some embodiments of the invention may use DM4. In this example, to a solution of Anti-Globo H monoclonal antibody 500 μL (2.9 mg/mL) in buffer (50 mM potassium phosphate, 50 mM sodium chloride, 2 mM EDTA; pH 6.5) was slowly added 58 μL SMCC-DM4 (5 mM in DMSO). The reaction mixture was stirred under argon at 37° C. and stirred for 20 hours. Desalt and concentrate the antibody preparation using the Amicon Ultra-15 centrifugal filter device with 30 kDa NMWL in pH 7.4 PBS buffer to give Anti-Globo H-SMCC-DM4 ADC 4

Example 5. Preparation of Anti-Globo H Antibody-MMAE Conjugates

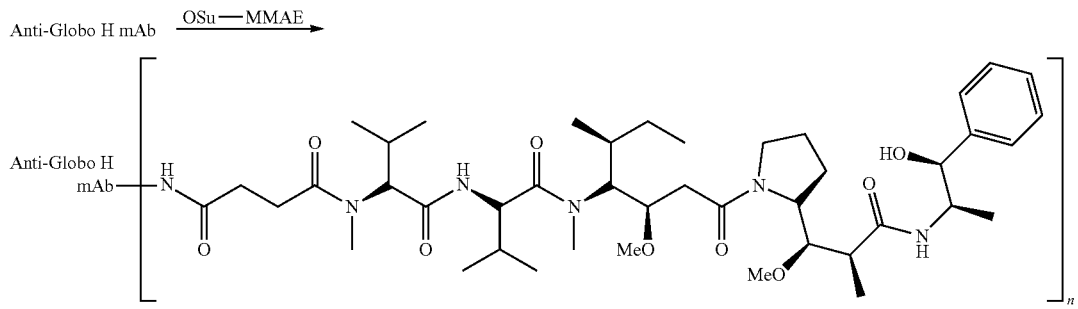

5

Monomethyl auristatin E (MMAE) is a antineoplastic agent; it inhibits cell division by blocking the polymerization of tubulins. It is derived from peptides occurring in marine shell-less mollusk (dolastatins). MMAE has been shown to be useful payloads for ADCs.

In this example, to a solution of Anti-Globo H monoclonal antibody 400 µL (5.0 mg/mL) in buffer (50 mM potassium phosphate, 50 mM sodium chloride, 2 mM EDTA, pH 6.5) was slowly added 40 µL OSu-MMAE (5 mM in DMSO). The reaction mixture was stirred under argon at 37° C. and stirred for 20 hours. Desalt and concentrate the antibody preparation using the Amicon Ultra-15 centrifugal filter device with 30 kDa NMWL in pH 7.4 PBS buffer to give Anti-Globo H-MMAE ADC 5.

Example 6. Preparation of Anti-Globo H Antibody-vc-MMAE Conjugates

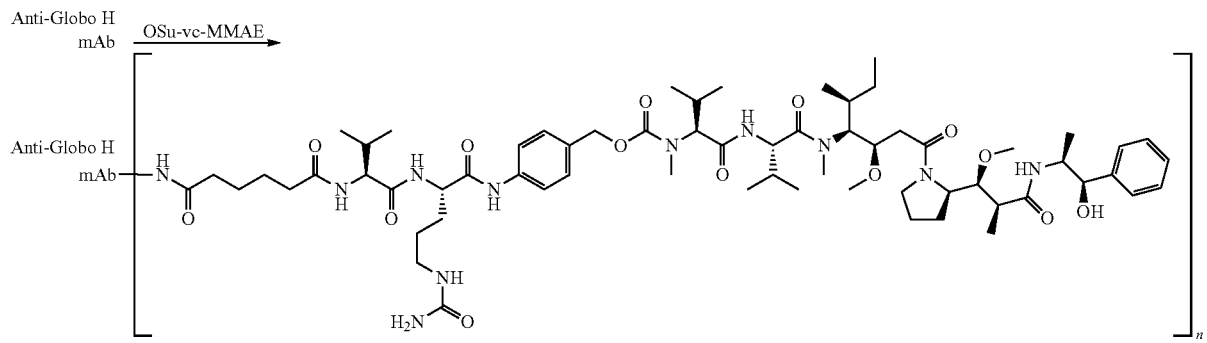

6

Linkers in ADCs may have significant impacts on the biological activities. For example, in vivo studies demonstrated that the peptide-linked conjugates induced regressions and cures of established tumor xenografts with therapeutic indices as high as 60-fold. These conjugates illustrate the importance of linker technology, drug potency and conjugation methodology in developing safe and efficacious mAb-drug conjugates for cancer therapy.

Some embodiments of the invention relate to MMAEs linked to antibodies via a lysosomally cleavable dipeptide, valine-citrulline (vc), which have been shown to improve ADC efficacies. In this example, to a solution of Anti-Globo H monoclonal antibody (400 µL (5.0 mg/mL)) in buffer (50 mM potassium phosphate, 50 mM sodium chloride, 2 mM EDTA; pH 6.5) was slowly added 40 µL OSu-vc-MMAE (5 mM in DMSO). The reaction mixture was stirred under argon at 37° C. and stirred for 20 hours. Desalt and concentrate the antibody preparation using the Amicon Ultra-15 centrifugal filter device with 30 kDa NMWL in pH 7.4 PBS buffer to give Anti-Globo H-vc-MMAE ADC 6.

Example 7. Preparation of Anti-Globo H Antibody-MMAF Conjugates

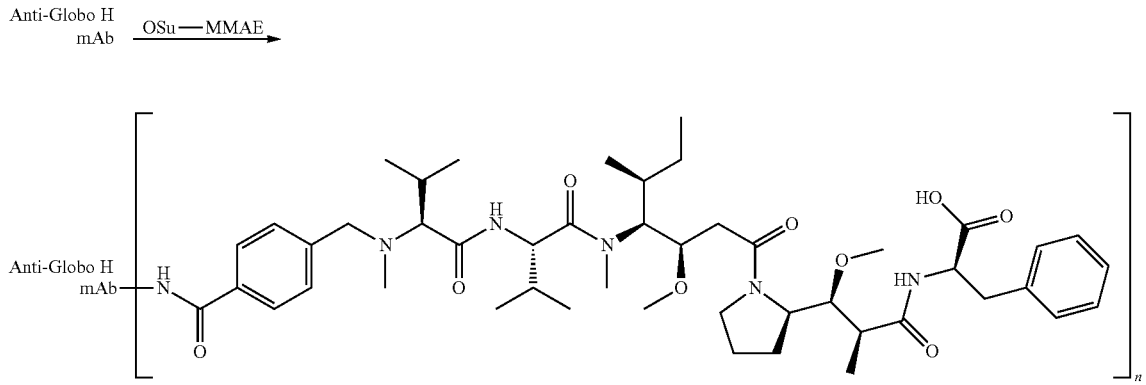

7

Some embodiments of the invention relate to ADCs containing Monomethyl auristatin F (MMAF), which is an analog of MMAE. To a solution of Anti-Globo H monoclonal antibody (400 μL (5.0 mg/mL) in buffer (50 mM potassium phosphate, 50 mM sodium chloride, 2 mM EDTA; pH 6.5) was slowly added 40 μL OSu-MMAF (5 mM in DMSO). The reaction mixture was stirred under argon at 37° C. and stirred for 20 hours. Desalt and concentrate the antibody preparation using the Amicon Ultra-15 centrifugal filter device with 30 kDa NMWL in pH 7.4 PBS buffer to give Anti-Globo H-MMAF ADC 7.

Example 8. Preparation of Anti-Globo H Antibody-4-Isothiocyanato-Phenyl-DTPA Conjugates

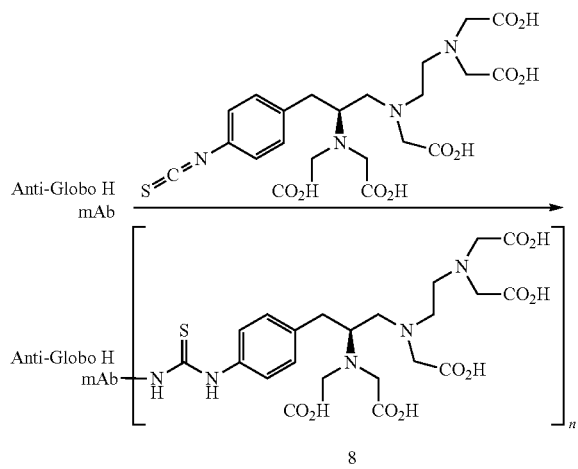

8

In addition to treatments, ADCs can also be used for diagnosis and/or imaging. Some embodiments of the invention relate to imaging reagents that can bind specifically to a target molecule. For example, the payloads of ADCs may contain a chelating functional group, which can be used to bind a selected metal, such as a radioactive transition metal, for imaging. Many chelating functional groups for diagnostic and/or imaging uses are known in the art, such as DTPA (Diethylenetriaminepentaacetic acid) or DOTA (1,4,7,10-tetraazacyclododecane-1,4,7,10-tetraacetic acid). DTPA is an aminopolycarboxylic acid having a diethylenetriamine backbone and 5 carboxyl groups. DTPA can be viewed as an expanded version of EDTA. Here, we will use DTPA as an example. One skilled in the art would appreciate that other chelating agents can also be used without departing from the scope of the invention.

In this example, to a solution of anti-Globo H monoclonal antibody 400 μL (5.0 mg/mL) in buffer (10 mM Sodium phosphate; pH 8.0) was slowly added 40 μL 4-isothiocyanato-phenyl-DTPA (5 mM in DMSO). The reaction mixture was stirred under argon at 37° C. and stirred for 20 hours. Desalt and concentrate the antibody preparation using the Amicon Ultra-15 centrifugal filter device with 30 kDa NMWL in pH 7.4 PBS buffer to give anti-Globo H-thiourea-4-phenyl-DTPA ADC 8.

Example 9. Preparation of Anti-Globo H Antibody-N-phenyladipamide-DTPA Conjugates

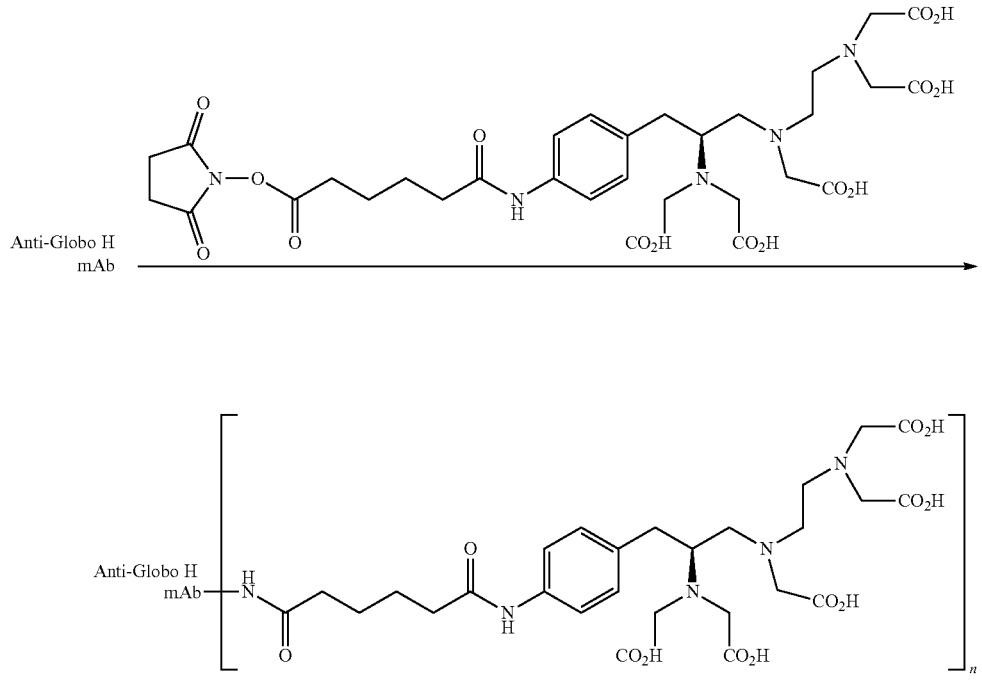

9

In this example, DPTA is linked to an antibody via a linker, adipamine. To a solution of Anti-Globo H monoclonal antibody 400 μL (5.0 mg/mL) in buffer (10 mM Sodium phosphate; pH 8.0) was slowly added 40 μL 6-OSu-N-phenylhexanamide-DPTA (5 mM in DMSO). The reaction mixture was stirred under argon at 37° C. and stirred for 20 hours. Desalt and concentrate the antibody preparation using the Amicon Ultra-15 centrifugal filter device with 30 kDa NMWL in pH 7.4 PBS buffer to give Anti-Globo H-N-phenylhexanamide-DPTA ADC 9.

Example 10. SDS-PAGE

The various ADCs of the invention may be analyzed with techniques known in the art, such as SDS-PAGE and HPLC. For example, the solution of anti-Globo H mAb and anti-Globo H ADC 3. (DCBD16001) obtained from Examples 1 and 3 were analyzed by using a 4-12% non-reducing and reducing SDS-PAGE gel followed by Coomassie brilliant blue staining. FIG. 1 shows that the ADC (DCB16001) retain the proper antibody structures—i.e., proper molecular weights under non-reduced and reduced conditions.

Example 11. PLRP-HPLC

Figure 2:
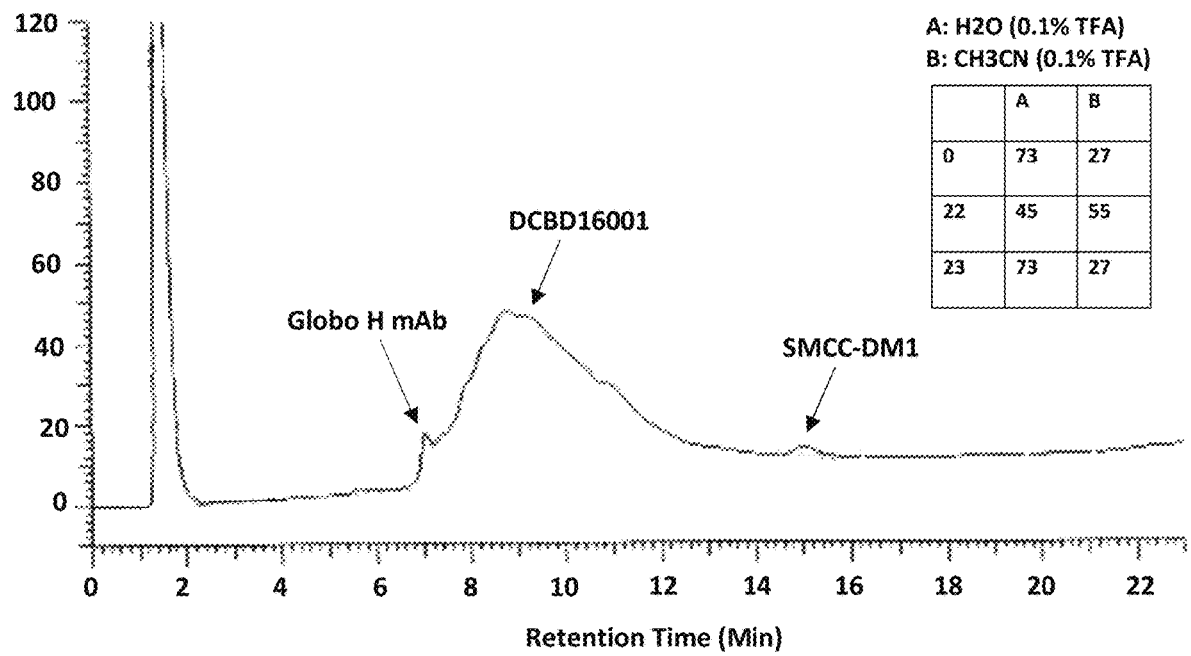
FIG. 2 shows an HPLC profile, indicating that the conjugation reaction between Globo H antibody and SMCC-DM1 went substantially complete and only residual amounts of Globo H antibody and SMCC-DM1 remained.

The various ADCs of the invention may also be analyzed with HPLC. FIG. 2 shows that the conjugation reaction went substantially complete and only residual amounts of Globo H antibody and SMCC-DM1 remained.

Example 12. Payload Coupling Assay

Evaluation the drug-to-antibody ratio (DAR) is important for monitoring of payload conjugation efficiency on target antibody. The drug-to-antibody ratio may affect the therapeutic efficacy of the anti-Globo H ADC products. Liquid chromatography-mass spectrometry (LC-MS) is the method of choice for determination of the drug-to-antibody ratio (DAR) and drug load distribution for lysine-linked antibody-drug conjugates (ADCs). The area percentage of a peak represents the relative distribution of the particular drug-loaded ADC species. The weighted average DAR is then calculated using the percentage peak area information and the drug load numbers.

Figure 3:
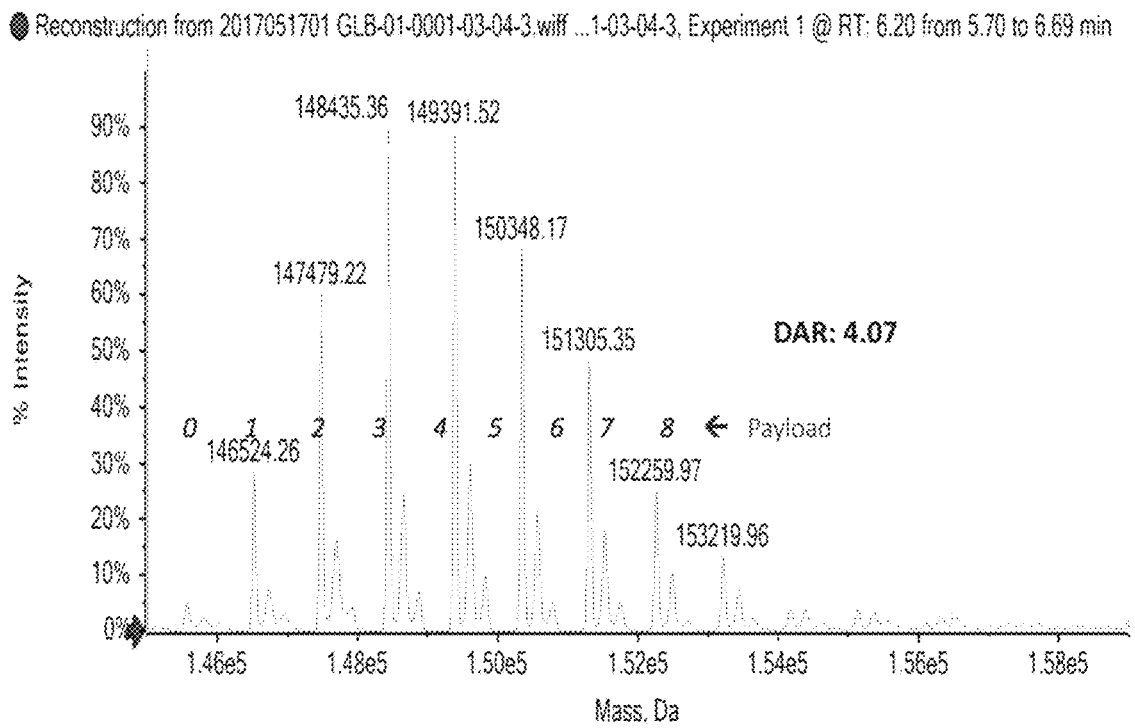
FIG. 3 illustrates one example of MS analysis of an ADC of the invention (DCB16001), which indicates a distribution of various numbers of drug attached to an antibody with the most abundant species having 1-8 drugs attached to an antibody. The average drug-to-antibody ratio (DAR) in this sample is 4.07.

FIG. 3 illustrates one example of MS analysis of an ADC of the invention (Anti-Globo H-SMCC-DM1 ADC 3. (DCBD16001)), which indicates a distribution of various numbers of drug attached to an antibody with the most abundant species having 1-8 drugs attached to an antibody. The average drug-to-antibody ratio (DAR) in this sample is 4.07. Having multiple copies of the drug attached to one antibody would ensure more efficient delivery of the drug into cells.

Example 13. Binding Affinity

The binding affinities of ADCs of the invention may be assessed with any suitable methods known in the art, such as BIAcore or ELISA. In this example, BIAcore is used to measure the affinities of an ADCs of the invention.

Briefly, to a flow solution of anti-Globo H ADC was prepared for binding kinetics studies. Ligand Globo H was immobilized on CM5 chip: First, Dilute the ligand (Globo H-amine) to 6 mg/mL in immobilization buffer (10 mM sodium acetate pH 4.5). General immobilization at 25° C. using a flow rate of 5 μL/min. Reagents for immobilization are provided in the amine coupling kit. Activation: EDC/NHS 7 minutes. Immobilization: flow time 720 seconds. Deactivation: 1.0M ethanolamine pH8.5 7 minutes. This procedure should result in response bound level about 200 RU on sensor chip CM5.

Then, the single-cycle kinetics assay was performed as followed: Biacore single-cycle kinetics (SCK) method provided with the software to obtain kinetics data. Choose Run: Method. Set the parameters as followed: Data collection rate: 1 Hz, Detection mode: Dual, Temperature: 25° C., Concentration unit: nM, Buffer A: HBS-EP+ buffer. Select the Start up and change the Number of replicates to 3. Select the Startup cycle and set the parameters as followed: Type: Low sample consumption, Contact time: 150 seconds, Dissociation time: 420 seconds, Flow rate: 50 μL/min, Flow path: Both. Select the Sample cycle and set the parameters as followed: Type: Single cycle kinetics, Concentration per cycle: 5, Contact time: 150 seconds, Dissociation time: 420 seconds, Flow rate: 50 μl min, Flow path: Both. Select the Regeneration and set the parameters as followed: Regeneration solution: 10 mM Glycine pH2.0/1.5 (v/v=1), Contact time: 45 seconds, Flow Rate: 30 μL/min, Flow path: Both. Select the Copy of the sample and set the parameters as above. Prepare samples: Dilute the analyte antibody DCBPR1101 in running buffer to 200 nM. Prepare the concentration series from the 200 nM sample: mix 200 μL of the 200 nM solution with 2000 μL running buffer to get the 100 nM solution. Continue the dilution series to obtain the following: 200, 100, 50, 25 and 12.5 nM. Prepare and position samples according to Rack Positions. Make sure everything is correct according to the Prepare Run Protocol and click Start to begin the experiment. Affinity binding curve fit using predefined model (1:1 binding) provided by Biacore T100 evaluation software 2.0.

Table 1 summarizes the results of the BIAcore assay for one ADC of the invention (DCBD16001). These results show that the ADCs of the invention can still bind specifically to the antigen (Globo H).

TABLE 1

| $k_{on}$ (1/Ms) | $k_{off}$ (1/s) | $K_D$ (M) | $R_{max}$ | Chi$^2$ |
| --- | --- | --- | --- | --- |
| 8.725E+4 | 1.427E−3 | 1.636E−8 | 365.6 | 7.04 |

Example 14. Cytotoxicity Assay

ADCs of the invention containing cytotoxic payloads may be used to kill target cells, such as killing cancer cells. For this assay, MCF-7, HCC-1428, BT-474 was obtained from ATCC. All cell lines were cultured in a suitable culture medium at 37° C. in a humidified incubator atmosphere of 5% $CO_2$. All cell lines were subcultured for at least three passage, cells were plated in 96-well black flat bottom plates (10,000 cells/100 μl/well for all cell lines) and allowed to adhere overnight at 37° C. in a humidified atmosphere of 5% $CO_2$.

ADCs were prepared from 1 ug/ul stock solution and diluted into appropriated working concentration 24 h after cell seeding. 20 mM test article was first diluted into the highest working concentrate with PBS. From this highest working concentrate, a serial three-fold dilution for eight points was performed with DMSO, and then diluted 100× further with culture medium. We detect 8 concentrates, the final concentration was ranging from 100 nM to 0.046 nM (DM-1) or 66.67 nM to 0.030 nM (DBCD16001, DCBPR1101). Final PBS concentration was 1%. Medium was then removed and replaced by fresh culture medium containing different concentrations of free DM1, DBCD16001, DCBPR1101 and 200 μl/well and the cells incubated for 72 hours. Pre-thaw Cell Titer-Glo reagent at room temperature for 48 hours. After this time point, medium was removed and 100 μl/well of Cell Titer-Glo reagent (Promega G7571, lot 0000182872) was added to the wells for 10 min at room temperature and the luminescent signal was measured using a CLARIOstar® High Performance Monochromator Multimode Microplate Reader. For all cellular assays, dose-response curves were generated using GraphPad Prism 6 three-parameter curve fitting.

The results from these assays are shown in the following TABLE 2. It is clear that ADC of the invention (i.e., DCBD16001) is effective in the killing of antigen (Globo H) expression cells (MCF-7 and HCC-1428), as compared to the antigen-negative cells (i.e., BT-474).

TABLE 2

| | CellTiter-Glo Cell Viability Assay | | |
|---|---|---|---|
| Relative $IC_{50}$ | Globo H-expressing cell | | Globo H-negative cell |
| Compound | MCF-7 | HCC-1428 | BT-474 |
| DCBD16001 (nM DM1 equivalents) | 39.0 | 7.5 | >333.0 |
| DCBPR1101 nM of Ab) | >66.6 | >66.6 | >66.6 |

Example 15. Internalization Assay

Receptor-mediated internalization of antibodies can provide cell-specific drug delivery. The internalization is necessary for some targeted therapies using ADC. It is known in the art that internalization of ADCs is both antibody-dependent and payload-dependent. That is, not all antibodies can provide delivery mechanism for ADCs. Similarly, different payloads on the same antibody may have dramatically different internalization efficiencies.

Internalization and degradation of anti-Globo H ADC and anti-Globo H antibody can be measured by flow cytometry. Two methods were used in this study, directly fluorescent-labeled on antibodies or use fluorescent-conjugated secondary antibodies to detect the primary antibodies left on the cell surface after internalization.

Briefly, MCF7 or HCC 1428 breast cancer cells were seeded in $1\times10^5$ cell/well. Next, 0.5-1 mg of fluorescent-labelled anti-Globo H antibody or anti-Globo H ADC was subjected in 100 μl of target cell (cell density $1\times10^6$/ml) in FACS buffer for 1 hour at 4° C. to enable specific binding of anti-Globo H antibody or anti-Globo H ADC to the cell surface targets. After incubation, the cells were washed three times with FACS buffer to removed unbound antibody. The cells were then incubated at 37° C. with 5% $CO_2$ for antibody internalization.

At different time points, the cells were dissociated with Trypsin and stained with fluorescent-conjugated anti-human IgG secondary antibodies for 5 min before being analyzed using Beckman flow cytometry system. For measurement of internalization and degradation of the indirectly labeled antibody or indirectly fluorescent-labeled secondary antibody, as compared with 4° C. control group (as antibody internalization background), the fluorescent intensity and cell binding percentage at each time point were analyzed by Beckman flow cytometric software. Each experiment was done in triplicate.

To study the internalization of anti-Globo H ADC and anti-Globo H antibody by fluorescence imaging, the cells were imaged on a DeltaVision® Core microscope using standard filter configurations. Briefly, MCF-7 or HCC1428 target cells were sub-cultured at $\sim 2\times10^5$ cells per well on 8-well glass coverslip bottom dishes (Nunc). After attachment, cells were incubated overnight at 37° C. with 10 nM anti-Globo H antibody or anti-Globo H ADC conjugated to Alexa-488. Before internalization, the cells were transfected with Rab5-mCherry or LAMP1-mApple plasmid for endosomal and lysosomal labelling with fluorescent markers LysoTracker. Cells were washed and imaged on a Deltavision deconvolution microscope to determine Alexa 488 and Alexa594 co-localization.

Figure 4:
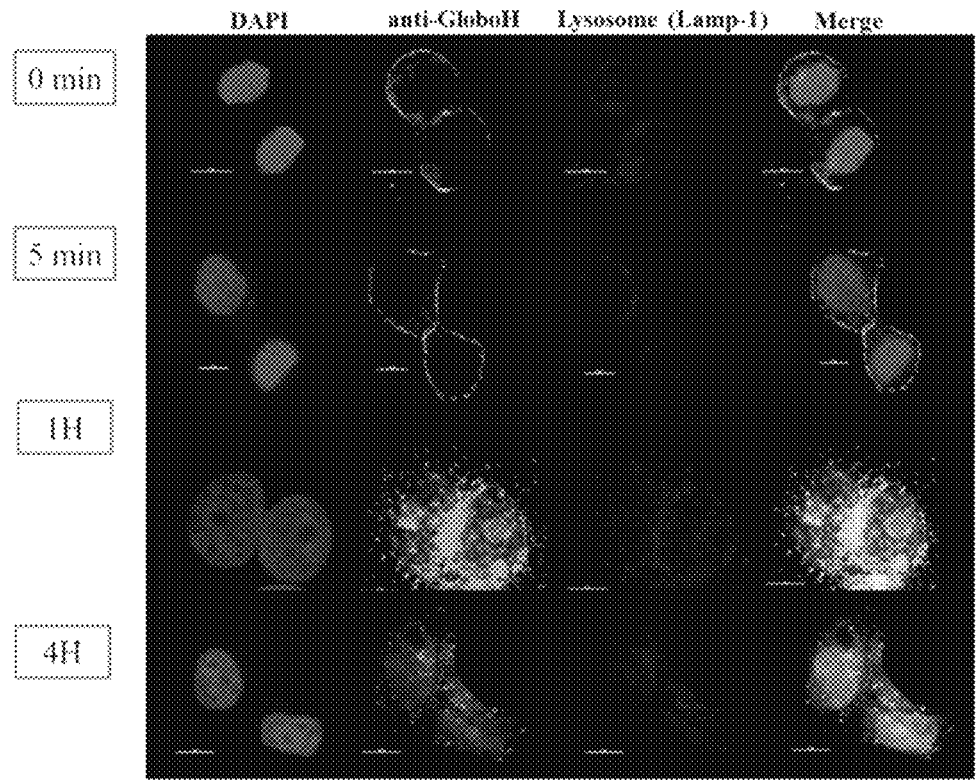
FIG. 4A and FIG. 4B show the results from fluorescence imaging of ADC internalization. Results indicate that ADCs of the invention can be internalized by cells expressing Glob H (e.g., MCF-7 (FIG. 4B) and HCC-1428 cells (FIG. 4A)).
Figure 4:
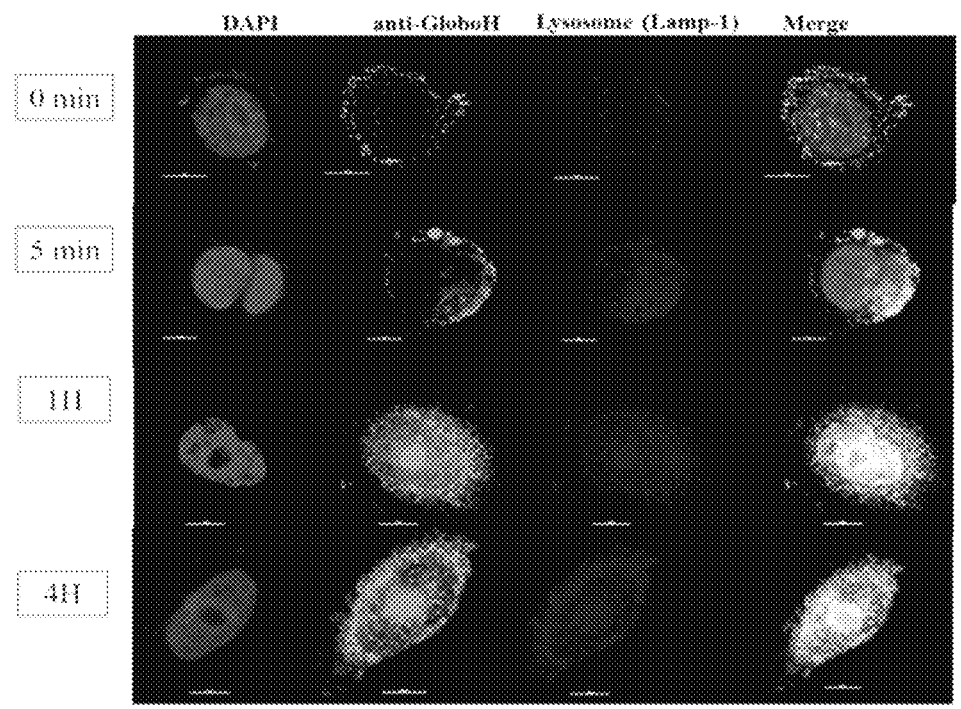

FIG. 4A and FIG. 4B show the results from these studies. Results indicate that ADCs of the invention can be internalized by cells expressing Glob H (e.g., MCF-7 (FIG. 4B) and HCC-1428 cells (FIG. 4A)).

Example 16. In Vivo PK

Figure 5:
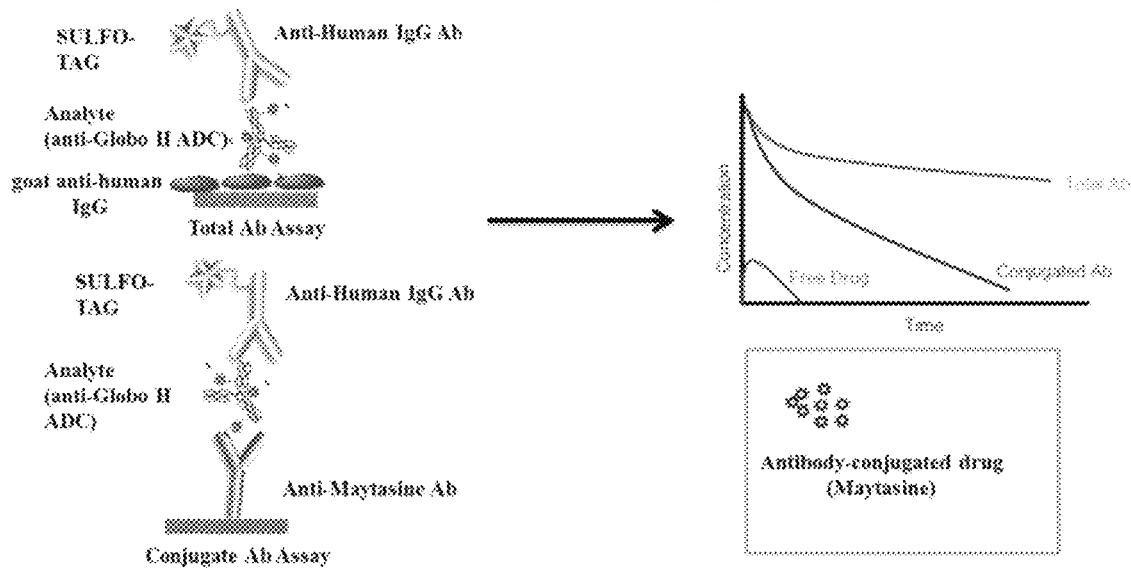
FIG. 5 shows a schematic diagram illustrating Meso Scale Discovery (MSD) Electrochemiluminescent assays for measuring total and conjugated anti-Globo H antibodies for in vivo pharmacokinetic studies of DCBD16001.

This study was used Meso Scale Discovery (MSD) Electrochemiluminescent (ECL) method for the pharmacokinetic analysis of DCBD16001 in BALB/c mice samples. The antibody MSD assay can measure both conjugated and unconjugated antibodies, as illustrated in FIG. 5. As illustrated in this example, or total antibody assay the plate is coated with goat anti-human IgG, which can capture all humanized antibodies (conjugated and unconjugated). For the conjugated antibody assay, the plate is coated with an antibody against the payload (drug), such as anti-Maytasine antibody shown in FIG. 5.

The BALB/c mice were administered at a dose level of 1 mg/kg via the tail vein. Blood samples were then obtained at different time points for determining concentrations of DCBD16001 in BALB/c mice by MESO QuickPlex SQ 120 method. The pharmacokinetic parameters of DCBD16001 were analyzed by noncompartmental analysis using Phoenix™ for WinNonlin Program, version 6.3.

FIG. 6 shows the results from the in vivo pharmacokinetic studies and the following TABLE 3 summarizes the results for the PK studies. Total antibody MSD assay: measures both conjugated and unconjugated antibody. Conjugated antibody MSD assay: measures conjugated antibody only. The in vivo half live of DCBD16001 is around 127 hours which is relative shorter than those of known therapeutic antibodies, suggesting that DCBD16001 could be washed out faster if serious side-effects occur.

TABLE 3

| Group | | $C_0$ (ng/mL) | $AUC_{(0-last)}$ (ng*hr/mL) | $AUC_{(0-\infty)}$ (ng*hr/mL) | MRT (hr) | $t_{1/2}$ (hr) | CL (mL/min/Kg) | $V_{ss}$ (L/Kg) |
|---|---|---|---|---|---|---|---|---|
| DCBD 16001 (N = 3) | Total | 5583 ± 249 | 275912 ± 6134 | 294825 ± 3005 | 158 ± 10.9 | 127 ± 9.11 | 0.057 ± 0.001 | 0.537 ± 0.038 |
| | Conjugated | 5750 ± 674 | 191078 ± 8925 | 193292 ± 8363 | 88.2 ± 6.80 | 79.3 ± 14.4 | 0.086 ± 0.004 | 0.457 ± 0.046 |

Example 17. Xenograft Model of Anti-Globo H ADC

Some embodiments of the invention relate to methods for diagnosis, imaging, and treatments of diseases, using antibodies in the ADCs as homing/targeting agents. The antibody portion will bind specifically to its target antigen, while the payload will provide the diagnostic/imaging or treatment reagents. Possible diagnostic/imaging reagents, for example, may include fluorescence moieties or radioactive probes, while treatment reagents, for example, may include cytotoxic agents or immune modulators (e.g., CD3).

In this particular example, the abilities of ADCs of the invention to treat cancers are assessed. Briefly, six to seven weeks-old male CB.17 SCID mice were purchased from BioLasco Taiwan Co., LTD. and quarantined for one week. During experiment period, 5 mice are housed in one cage. All animals are hosted in the Da-Hu animal facility in a 12-h light/12-h dark cycle at 19-25° C. Animals have free access to rodent pellet foods and water ad libitum. The experimental protocol of animal study was reviewed and approved by the Institutional Animal Care and Use Committee, DCB.

Mice were inoculated with a 17-β-estradiol pellet (0.18 mg/pellet, 60-day release; Innovative Research of America, USA) 7-days prior to injection of tumor cells. HCC1428 breast cancer cells used for implantation were harvested during log phase growth and resuspended in phosphate buffered saline (PBS). Each mouse was injected subcutaneous (s.c.) in the flank with $1\times10^7$ cells of HCC1428 in 0.15 mL of a 50% Matrigel solution (BD Biosciences, Mass., USA). When the average tumor volume had reached 250 mm$^3$, the mice were randomly divided into 8 groups. Group 1 receives PBS, serving as a control group for calculation of tumor growth inhibition rate. Group 2-5 receives DCBD16001 at 3 mg/kg (mpk) twice per week, 10 mpk twice per week, 20 mpk once per week, and 30 mg/kg each on day 1 and day 11, respectively. Group 6 receives naked antibody PR1101 (without payload) at 10 mpk twice per week. Mice in Group 7 receive isotype antibody at 10 mpk twice per week, serving as a negative control group. Mice in Group 8 receive paclitaxel at 10 mpk once per week, serving as a positive-treatment control group. Mice treated with vehicle, DCBD16001, naked antibody, and isotype antibody were by iv injection, while Paclitaxel was given by ip injection.

Tumor volumes were measured three times per week using calipers and estimated using the following formula: Tumor Volume=$(w^2\times l)/2$, where w=width and l=length in diameter (mm) of the tumor. The percentages of tumor growth inhibition (TGI) were calculated using the following formula: % TGI=$[1-(T/C)]\times 100\%$, where T and C represent the mean tumor volumes of the treatment group and the control group, respectively.

Animals were weighed three times weekly until the completion of the study. The body weight changes were calculated as percentage increases in the body weights, as compared with the initial body weights.

FIG. 7 illustrates the experimental protocols and treatment schemes. In this experiment, HCC1428 cells, which is a breast cancer cell line, are used. These cells express Glob H on their surfaces.

Figure 8:
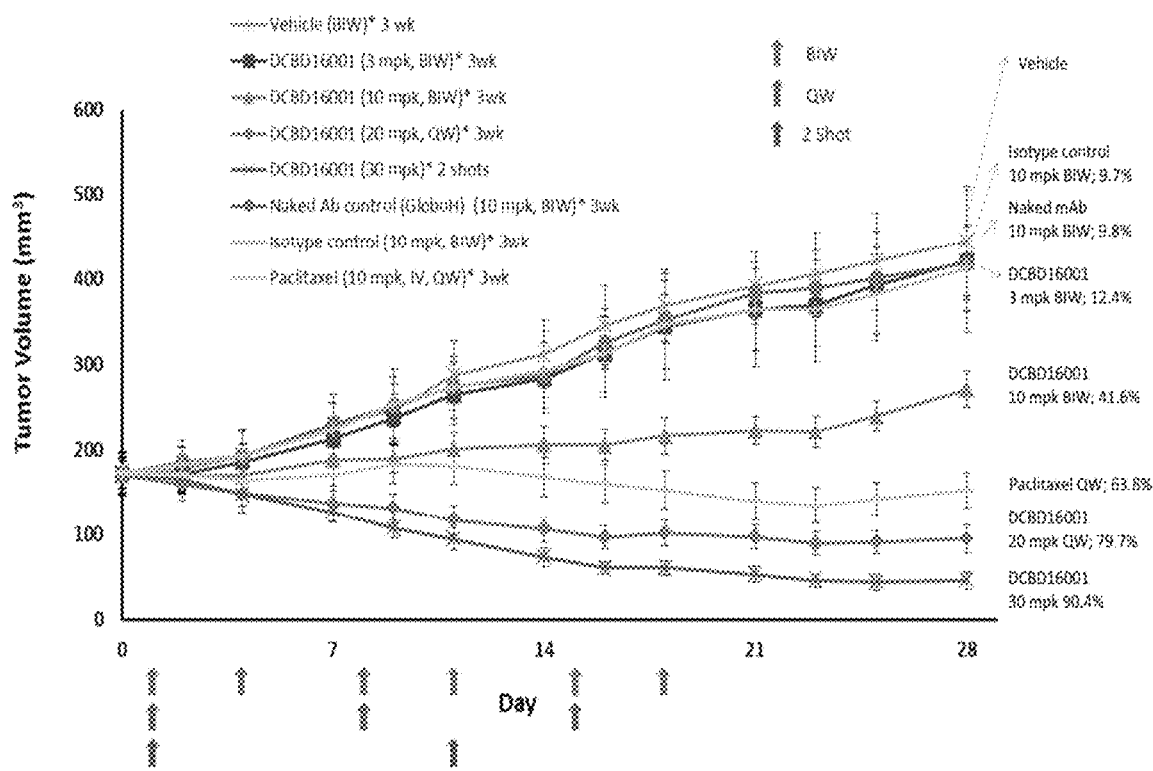
FIG. 8 shows tumor growth inhibition in HCC-1428 xenograft model.

FIG. 8 shows the results of the in vivo xenograft tumor treatment studies. As shown, ADC of the invention (DCBD16001) at 10 mg/kg, 20 mg/kg, and 30 mg/kg are significantly more effective than the naked antibody (anti-Globo H antibody). The result indicates the effectiveness of the ADC of the invention. The significantly improved efficacy is due to the coupled payloads, which may enhance the cytotoxicities and/or improve pharmacokinetics.

Interestingly, the treatment with DCBD16001 at 30 mpg on day 1 and day 11 (for a total dose of 60 mg/kg) is the most effective, significantly more effective than at 10 mg/kg twice per week (a total dose of 60 mg/kg). This result indicates that at a higher single-injection dose and a longer administration interval (10 days), the ADC is more effective. The fact that under the same total dose, the longer administration intervals (e.g., 10 days) produced the better results is unexpected. This may suggest for anti-Globo H ADC, higher Cmax may be more important than higher AUC.

Figure 9:
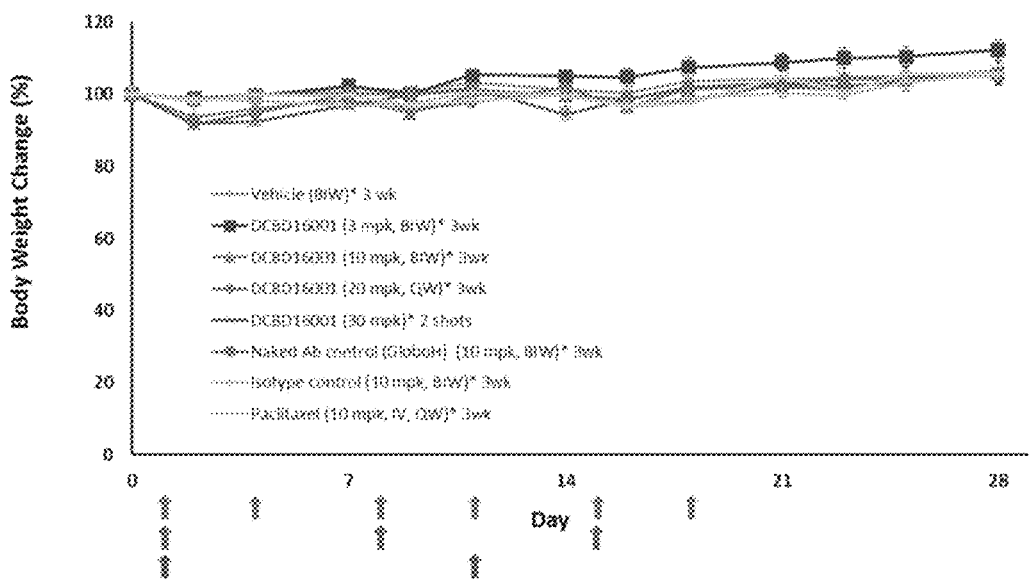
FIG. 9 shows body weight changes of mice during treatments in the experiment of FIG. 8.

That the tumor growth suppressions result from enhanced killing of tumor cells or inhibition of tumor cell growth is corroborated by the fact that the body weights of the mice do not have appreciable changes among the different treatment groups, as shown in FIG. 9.

The above examples clearly illustrate various methods for obtaining and characterizing ADCs of the invention, as well as the effectiveness of the ADCs of the invention in treating cancers. Even though embodiments of the invention are illustrated with a limited number of examples, one skilled in the art would appreciate that other variations and modifications are possible without departing from the scope of the invention. Accordingly, the scope of protection of the invention should only be limited by the attached claims.

---

What is claimed is:

1. An immunoconjugate that binds specifically to Globo H, comprising an anti-Globo H antibody or an antigen-binding fragment thereof, and a cytotoxic agent or a label, wherein
the immunoconjugate has the formula: Ab–(L–D)$_m$,
wherein
the Ab is the anti-GLOBO H antibody, or the antigen-binding fragment,
L is a linker or a direct bond,
D is the cytotoxic agent or the label, and
m is an integer from 1 to 8,
wherein the antibody comprises heavy chain variable domain having three complementarity determining regions consisting of HCDR1, HCDR2 and HCRD3, and a light chain variable domain having three complementarity determining regions consisting of LCDR1, LCDR2 and LCDR3, wherein the sequence of HCDR1 is GYISSDQILN (SEQ ID NO:1), the sequence of HCDR2 is RIYPVTGVTQYXHKFVG (SEQ ID NO:2), wherein X is any amino acid, the sequence of HCDR3 is GETFDS (SEQ ID NO: 3), the sequence of LCDR1 is KSNQNLLX'SGNRRYZLV (SEQ ID NO:4) wherein X' is F, Y or W and Z is C, G, S or T, the sequence of LCDR2 is WASDRSF (SEQ ID NO:5) and the sequence of LCDR3 is QQHLDIPYT (SEQ ID NO:6).

2. The immunoconjugate according to claim 1, wherein the antibody is a monoclonal antibody.

3. The immunoconjugate according to claim 1, wherein the antibody is a humanized antibody.

4. The immunoconjugate according to claim 1, wherein the cytotoxic agent is a maytansinoid 1 (DM1), maytansinoid 4 (DM4), monomethyl auristatin E (MMAE), monomethyl auristatin F (MMAF), or paclitaxel.

5. The immunoconjugate according to claim 1, wherein D is a diagnostic or imaging label.

6. A method for treating a cancer, comprising administering to a subject having a cancer expressing a Globo H antigen a pharmaceutical comprising the immunoconjugate according to claim 1, wherein D is a cytotoxic agent.

7. The method according to claim 6, wherein the antibody is a monoclonal antibody.

8. The method according to claim 6, wherein the antibody is a humanized antibody.

9. The method according to claim 8, wherein the cytotoxic agent is maytansinoid 1 (DM1), maytansinoid 4 (DM4), monomethyl auristatin E (MMAE), monomethyl auristatin F (MMAF), or paclitaxel.

10. The method of claim 6, wherein the cancer is an epithelial cell cancer.

11. The method of claim 10, wherein the cancer is breast cancer, colon cancer, ovarian cancer, pancreatic cancer, lung cancer, or prostate cancer.

12. A method for diagnosing or imaging cells or tissues expressing Globo H, comprising contacting a sample of cells or tissue with the immunoconjugate according to claim 5.

* * * * *